US012109072B2

(12) United States Patent
Drown et al.

(10) Patent No.: US 12,109,072 B2
(45) Date of Patent: Oct. 8, 2024

(54) PROTECTING NON-TARGET TISSUE DURING ABLATION PROCEDURES AND RELATED SYSTEMS AND METHODS

(71) Applicant: Medtronic Navigation, Inc., Louisville, CO (US)

(72) Inventors: Christine Drown, Louisville, CO (US); Rebecca Vincelette, Louisville, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 109 days.

(21) Appl. No.: 17/325,858

(22) Filed: May 20, 2021

(65) Prior Publication Data

US 2021/0393365 A1  Dec. 23, 2021

Related U.S. Application Data

(60) Provisional application No. 63/042,288, filed on Jun. 22, 2020.

(51) Int. Cl.
*A61B 90/00* (2016.01)
*A61B 18/00* (2006.01)
*A61B 18/20* (2006.01)

(52) U.S. Cl.
CPC .............. *A61B 90/04* (2016.02); *A61B 18/20* (2013.01); *A61B 2018/00446* (2013.01);
(Continued)

(58) Field of Classification Search
CPC . A61B 90/04; A61B 18/20; A61B 2090/0409; A61B 2018/004466
See application file for complete search history.

(56) References Cited

U.S. PATENT DOCUMENTS 9,839,477 B2    12/2017  Brannan
2014/0074078 A1*  3/2014  Kumar ................... A61B 34/10
                                                    606/15
(Continued)

FOREIGN PATENT DOCUMENTS

WO    2019069135    4/2019

OTHER PUBLICATIONS

International Search Report and Written Opinion dated Sep. 14, 2021 for PCT/US2021/033461.

*Primary Examiner* — Mallika D Fairchild
*Assistant Examiner* — Thien Jason Tran
(74) *Attorney, Agent, or Firm* — Sheridan Ross P.C.

(57) ABSTRACT

Systems and methods for protecting non-target tissue from damage during a medical procedure for disrupting target tissue via heat application are disclosed. Data associated with the target tissue to be disrupted may be received. Based on the received data, one or more non-target objects of tissue that may be affected by the applied heat are identified. Both a temperature threshold and thermal dose threshold for each of the one or more non-target objects may be generated. Both the temperature and the thermal dose of each of the one or more non-target objects may be evaluated during performance of the medical procedure. A response may be generated when either the evaluated temperature of any of the one or more non-target objects reaches the corresponding temperature threshold or the thermal dose of any of the one or more non-target objects reaches the corresponding thermal dose threshold.

21 Claims, 5 Drawing Sheets

(52) U.S. Cl.
CPC ............ *A61B 2018/00452* (2013.01); *A61B 2018/00511* (2013.01); *A61B 2018/00529* (2013.01); *A61B 2018/00577* (2013.01); *A61B 2018/00666* (2013.01); *A61B 2018/00714* (2013.01); *A61B 2090/0409* (2016.02); *A61B 2090/049* (2016.02)

(56) References Cited

U.S. PATENT DOCUMENTS

| | | | |
|---|---|---|---|
| 2014/0180273 A1* | 6/2014 | Nair | A61B 18/1492 606/34 |
| 2015/0359603 A1 | 12/2015 | Levy et al. | |
| 2019/0008572 A1 | 1/2019 | Lalonde et al. | |
| 2019/0247120 A1 | 8/2019 | Greenwood et al. | |
| 2019/0262074 A1 | 8/2019 | Kusumoto | |
| 2019/0343579 A1 | 11/2019 | Harikrishna et al. | |
| 2020/0139158 A1 | 5/2020 | Levy et al. | |
| 2020/0146743 A1* | 5/2020 | Defosset | A61B 18/1206 |

* cited by examiner

PROTECTING NON-TARGET TISSUE DURING ABLATION PROCEDURES AND RELATED SYSTEMS AND METHODS

RELATED APPLICATION

This application claims priority to U.S. Provisional Application No. 63/042,288, filed on Jun. 22, 2020 and titled, "Protecting Non-Target Tissue During Ablation Procedures and Related Systems and Methods," which is hereby incorporated by reference in its entirety.

TECHNICAL FIELD

The present disclosure relates generally to the field of medical devices. More particularly, some embodiments relate to tissue ablation devices and related systems and methods.

BRIEF DESCRIPTION OF THE DRAWINGS

The written disclosure herein describes illustrative embodiments that are non-limiting and non-exhaustive. Reference is made to certain of such illustrative embodiments that are depicted in the figures.

DETAILED DESCRIPTION

Tissue ablation devices can be used to treat problematic tissue within the body of a patient (e.g., a tumor on the brain of a patient). For instance, as an initial step of a tissue ablation procedure, a surgeon may use an image of tissue (e.g., captured using Magnetic Resonance Imaging (MRI)) that includes the area to be treated (also referred to herein as target tissue) in conjunction with computer software to identify the target tissue and create a surgical plan that allows for treating the target tissue while attempting to avoid any healthy surrounding tissue or critical structures (e.g., the patient's brain stem). In the example of treating a patient's brain tissue, a small entry (e.g., between 3 and 5 millimeters) can be made in the skull of the patient. An MRI compatible bone anchor may then be fixed to the entry to allow for the introduction and securing of a laser applicator.

The laser applicator can then be inserted into the target tissue. The laser applicator may include a laser fiber that is then connected to a laser energy source. The patient is placed in the MRI and imaged in preparation for the destruction of the target. The operator (e.g., a physician) can then review new images captured using the MRI to verify that the laser applicator is positioned properly within the target tissue. A low-power test pulse can be delivered as a second confirmation of precise placement of the laser applicator. The laser power is then increased causing light energy to be absorbed by the target tissue, thus heating and disrupting the target tissue.

While the example above relates specifically to performing such ablation with respect to the brain, ablation procedures associated with the prostate, kidney, liver, cardiovascular thoracic surgery, dermatology, ear-nose-throat surgery, gastroenterology, general surgery, gynecology, head and neck surgery, neurosurgery, plastic surgery, orthopedics, pulmonology, radiology, and urology may be similarly applicable when practicing the principles described herein. Similarly, the principles described herein may be equally applicable to any procedure where the temperature of tissue is to be monitored ((e.g., laser ablation, High-Intensity Focused Ultrasound (HIFU), and so forth). Regardless of the location/type of such tissue or the exact type of procedure, when disrupting problematic tissue using heat, a number of issues can arise. Notably, tissue damage is dependent on both temperature and time. Accordingly, while tissue will necrotize more quickly when higher temperatures are applied, even lower temperatures can damage tissue when applied for relatively long periods of time. As such, tissue near the problematic tissue that is being purposely destroyed can also be unintentionally damaged by either high temperatures or lower temperature heat applied for long periods of time. Such issues can be particularly problematic when critical tissue is located near the tissue to be disrupted (e.g., the brain stem near a tumor to be necrotized).

Some introductory discussion of a computing system will be described with respect to FIG. 1. Then, protecting non-target tissue from damage during a medical procedure for disrupting tissue through the application of heat to a target tissue will be described with respect to FIGS. 2 through 5.

Computing systems are now increasingly taking a wide variety of forms. Computing systems may, for example, be handheld devices, appliances, laptop computers, desktop computers, mainframes, distributed computing systems, datacenters, or even devices that have not conventionally been considered a computing system, such as wearables (e.g., glasses). In this description and in the claims, the term "computing system" is defined broadly as including any device or system (or combination thereof) that includes at least one physical and tangible processor, and a physical and tangible memory capable of having thereon computer-executable instructions that may be executed by a processor. The memory may take any form and may depend on the nature and form of the computing system. A computing system may be distributed over a network environment and may include multiple constituent computing systems.

Figure 1:
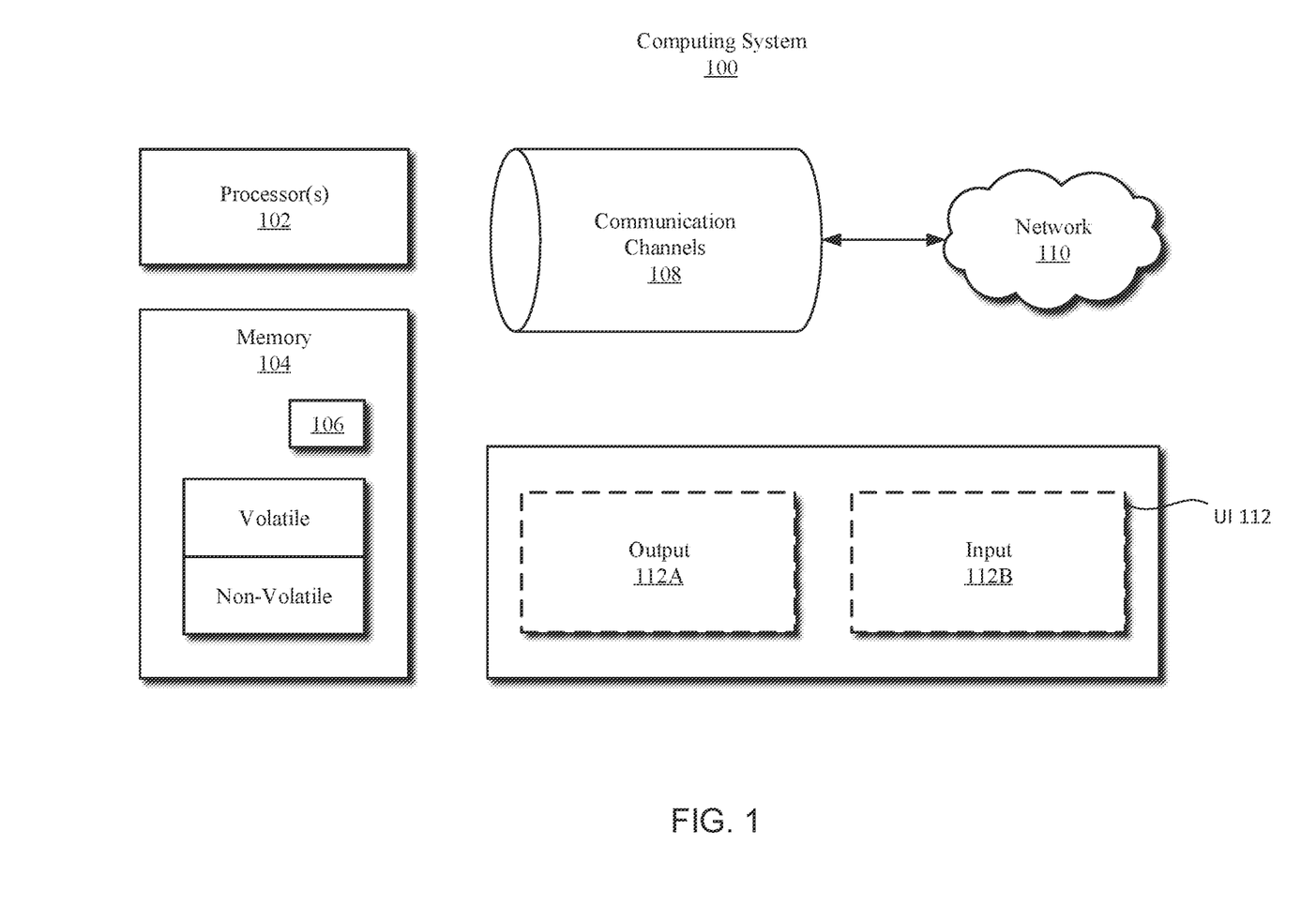
FIG. 1 illustrates an example computer architecture, according to one embodiment, that facilitates operation of the principles described herein.

As illustrated in FIG. 1, in its most basic configuration, a computing system 100 typically includes at least one hardware processing unit 102 and memory 104. The memory 104 may be physical system memory, which may be volatile, non-volatile, or some combination of the two. The term "memory" may also be used herein to refer to non-volatile mass storage such as physical storage media. If the computing system is distributed, the processing, memory and/or storage capability may be distributed as well.

The computing system 100 also has thereon multiple structures often referred to as an "executable component". For instance, the memory 104 of the computing system 100 is illustrated as including executable component 106. The term "executable component" is the name for a structure that is well understood to one of ordinary skill in the art in the field of computing as being a structure that can be software, hardware, or a combination thereof. For instance, when implemented in software, one of ordinary skill in the art would understand that the structure of an executable component may include software objects, routines, methods, and so forth, that may be executed on the computing system, whether such an executable component exists in the heap of a computing system, or whether the executable component exists on computer-readable storage media.

In such a case, one of ordinary skill in the art will recognize that the structure of the executable component exists on a computer-readable medium such that, when interpreted by one or more processors of a computing system (e.g., by a processor thread), the computing system is caused to perform a function. Such structure may be computer-readable directly by the processors (as is the case if the executable component were binary). Alternatively, the structure may be structured to be interpretable and/or compiled (whether in a single stage or in multiple stages) so as to generate such binary that is directly interpretable by the processors. Such an understanding of example structures of an executable component is well within the understanding of one of ordinary skill in the art of computing when using the term "executable component".

The term "executable component" is also well understood by one of ordinary skill as including structures that are implemented exclusively or near-exclusively in hardware, such as within a field programmable gate array (FPGA), an application specific integrated circuit (ASIC), or any other specialized circuit. Accordingly, the term "executable component" is a term for a structure that is well understood by those of ordinary skill in the art of computing, whether implemented in software, hardware, or a combination. In this description, the terms "component", "service", "engine", "module", "control", or the like may also be used. As used in this description and in the case, these terms (whether expressed with or without a modifying clause) are also intended to be synonymous with the term "executable component", and thus also have a structure that is well understood by those of ordinary skill in the art of computing.

In the description that follows, embodiments are described with reference to acts that are performed by one or more computing systems. If such acts are implemented in software, one or more processors (of the associated computing system that performs the act) direct the operation of the computing system in response to having executed computer-executable instructions that constitute an executable component. For example, such computer-executable instructions may be embodied on one or more computer-readable media that form a computer program product. An example of such an operation involves the manipulation of data.

The computer-executable instructions (and the manipulated data) may be stored in the memory 104 of the computing system 100. Computing system 100 may also contain communication channels 108 that allow the computing system 100 to communicate with other computing systems over, for example, network 110.

While not all computing systems require a user interface, in some embodiments, the computing system 100 includes a user interface 112 for use in interfacing with a user. The user interface 112 may include output mechanisms 112A as well as input mechanisms 112B. The principles described herein are not limited to the precise output mechanisms 112A or input mechanisms 112B as such will depend on the nature of the device. However, output mechanisms 112A might include, for instance, speakers, displays, tactile output, holograms and so forth. Examples of input mechanisms 1128 might include, for instance, microphones, touchscreens, holograms, cameras, keyboards, mouse of other pointer input, sensors of any type, and so forth.

Embodiments described herein may comprise or utilize a special purpose or general-purpose computing system including computer hardware, such as, for example, one or more processors and system memory, as discussed in greater detail below. Embodiments described herein also include physical and other computer-readable media for carrying or storing computer-executable instructions and/or data structures. Such computer-readable media can be any available media that can be accessed by a general purpose or special purpose computing system. Computer-readable media that store computer-executable instructions are physical storage media. Computer-readable media that carry computer-executable instructions are transmission media. Thus, by way of example, and not limitation, embodiments of the invention can comprise at least two distinctly different kinds of computer-readable media: storage media and transmission media.

Computer-readable storage media includes RAM, ROM, EEPROM, CD-ROM or other optical disk storage, magnetic disk storage or other magnetic storage devices, or any other physical and tangible storage medium which can be used to store desired program code means in the form of computer-executable instructions or data structures and which can be accessed by a general purpose or special purpose computing system.

A "network" is defined as one or more data links that enable the transport of electronic data between computing systems and/or modules and/or other electronic devices. When information is transferred or provided over a network or another communications connection (either hardwired, wireless, or a combination of hardwired or wireless) to a computing system, the computing system properly views the connection as a transmission medium. Transmissions media can include a network and/or data links which can be used to carry desired program code means in the form of computer-executable instructions or data structures and which can be accessed by a general purpose or special purpose computing system. Combinations of the above should also be included within the scope of computer-readable media.

Further, upon reaching various computing system components, program code means in the form of computer-executable instructions or data structures can be transferred automatically from transmission media to storage media (or vice versa). For example, computer-executable instructions or data structures received over a network or data link can be buffered in RAM within a network interface module (e.g., a "NIC"), and then eventually transferred to computing system RAM and/or to less volatile storage media at a computing system. Thus, it should be understood that storage media can be included in computing system components that also (or even primarily) utilize transmission media.

Computer-executable instructions comprise, for example, instructions and data which, when executed at a processor, cause a general purpose computing system, special purpose computing system, or special purpose processing device to perform a certain function or group of functions. Alternatively, or in addition, the computer-executable instructions may configure the computing system to perform a certain function or group of functions. The computer executable instructions may be, for example, binaries or even instructions that undergo some translation (such as compilation) before direct execution by the processors, such as intermediate format instructions such as assembly language, or even source code.

Those skilled in the art will appreciate that the invention may be practiced in network computing environments with many types of computing system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, datacenters, wearables (such as glasses) and the like. The invention may also be practiced in distributed system environments where local and remote computing systems, which are linked (either by hardwired data links, wireless data links, or by a combination of hardwired and wireless data links) through a network, both perform tasks. In a distributed system environment, program modules may be located in both local and remote memory storage devices.

Those skilled in the art will also appreciate that the invention may be practiced in a cloud computing environment. Cloud computing environments may be distributed, although this is not required. When distributed, cloud computing environments may be distributed internationally within an organization and/or have components possessed across multiple organizations. In this description and the following claims, "cloud computing" is defined as a model for enabling on-demand network access to a shared pool of configurable computing resources (e.g., networks, servers, storage, applications, and services). The definition of "cloud computing" is not limited to any of the other numerous advantages that can be obtained from such a model when properly deployed.

Figure 2:
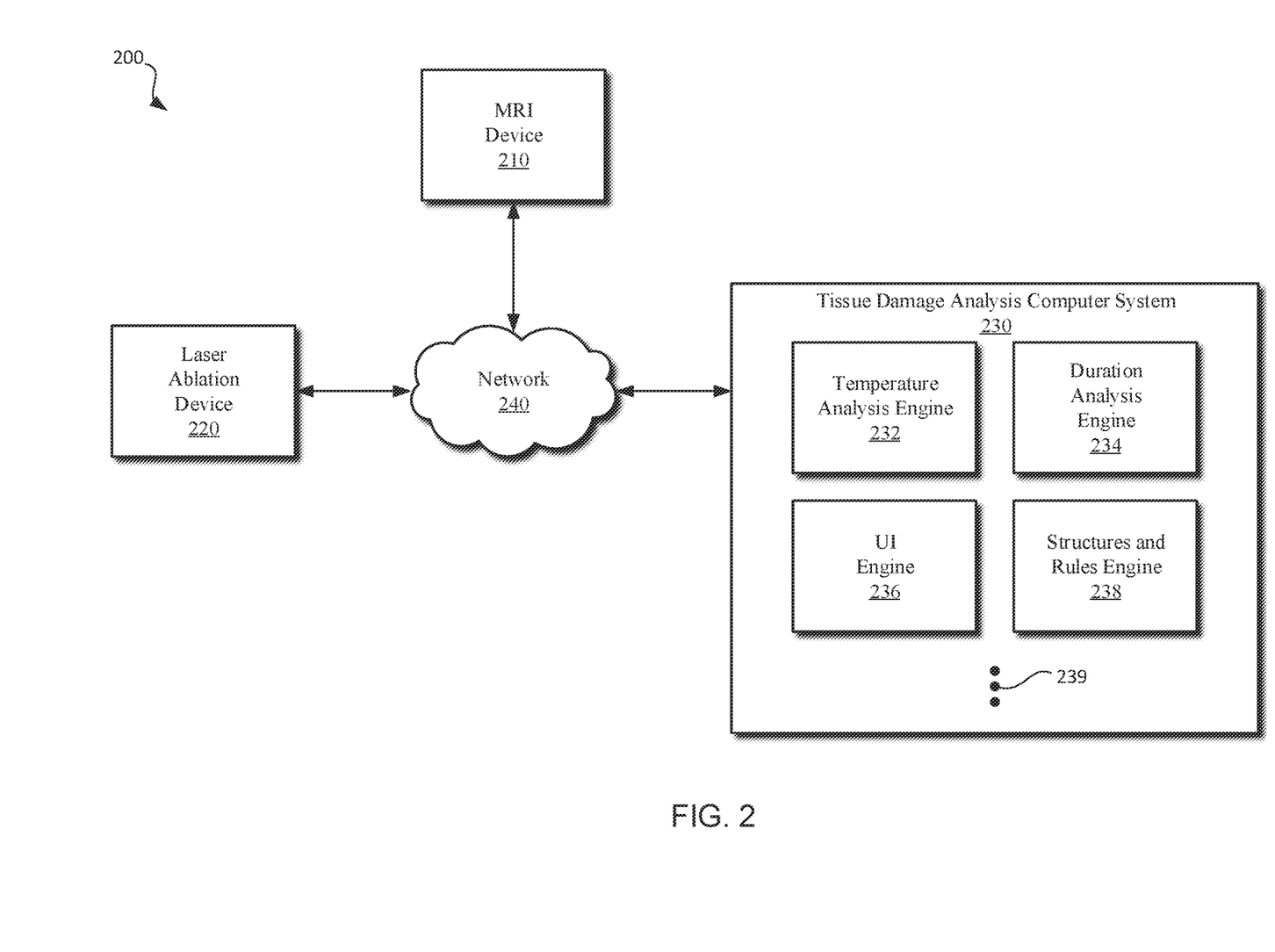
FIG. 2 illustrates an example environment, according to one embodiment, for protecting non-target tissue from damage during a medical procedure for disrupting tissue via heat application.

Accordingly, FIG. 2 illustrates an environment 200 for protecting non-target tissue from damage during a medical procedure for disrupting tissue via heat application (e.g., laser ablation procedures, HIFU procedures, and so forth). As illustrated, the environment 200 may include various devices, computer systems, engines, functional blocks, and components, including an MRI device 210, laser ablation device 220, a tissue damage analysis computer system 230, and a network 240, each of which may also include additional engines, functional blocks, and components. The various devices, computer systems, engines, components, and/or functional blocks of the environment 200 may include functionality that is implemented at least in part on a local computer system or on a distributed computer system that includes elements resident in the cloud or that implement aspects of cloud computing (e.g., one of the various illustrated engines may be implemented locally, while one other engine may be implemented remotely). In addition, the various devices, computer systems, engines, functional blocks, and/or components of the environment 200 may include functionality that is implemented as software, hardware, or a combination of software and hardware.

Notably, the configuration of the environment 200 illustrated in FIG. 2 is shown only for exemplary purposes. As such, the environment 200 may include more or less than the devices, computer systems, engines, functional blocks, and/ or components illustrated in FIG. 2. As an example, the tissue damage analysis computer system 230 may comprise part of the MRI device 210 in some embodiments. Regardless of the exact configuration, each of the MRI device 210, the laser ablation device 220, and the tissue damage analysis computer system 230 may communicate with one another via the network 240, which network may utilize any number of wired and/or wireless communication technology, as further described with respect to FIG. 1. In addition, each of the MRI device 210, the laser ablation device 220, and the tissue damage analysis computer system 230 may correspond to, or include, a computer system such as computer system 100, as described with respect to FIG. 1. For instance, each of the MRI device 210, the laser ablation device 220, and the tissue damage analysis computer system 230 may access and/or utilize a processor and memory, such as the processor 102 and the memory 104 of FIG. 1, as needed to perform their various functions.

As briefly described, the environment 200 may include the MRI device 210. The MRI device 210 may comprise any type of MRI device that is capable of generating images using Magnetic Resonance Imaging technology. For instance, the MRI device 210 may comprise a closed MRI machine, an open MRI machine, a 3 Tesla MRI machine, and so forth.

As shown in FIG. 2, the environment 200 also includes the laser ablation device 220, which is configured to necrotize or damage selected tissue of a patient. As shown with more specificity in FIG. 3, the laser ablation device 220 may include a laser applicator 322, a laser fiber 324, and a laser energy source 326. The laser applicator 322 is configured to be placed within or near the tissue to be damaged/necrotized and facilitate the provision of laser energy that is absorbed by such tissue. In particular, the laser applicator may be connected to the laser fiber 324 and ultimately, the laser energy source 326. Accordingly, the laser energy source may provide laser energy that is transmitted via the laser fiber and the laser applicator to the target tissue to be disrupted.

As briefly described, while laser ablation is discussed frequently herein, the principles discussed throughout this disclosure may be equally applicable to any procedure where the temperature of tissue is to be monitored. For instance, HIFU procedures may similarly benefit from the principles described herein. Regardless of the location/type of such tissue or the exact type of procedure, when disrupting problematic tissue using heat, a number of issues can arise. Notably, tissue damage is dependent on both temperature and time. Accordingly, while tissue will necrotize more quickly when higher temperatures are applied, even lower temperatures can damage tissue when applied for relatively long periods of time. As such, tissue near target tissue can also be unintentionally damaged by either high temperatures or lower temperature heat applied for long periods of time. Such issues can be particularly problematic when critical tissue is located near the tissue to be disrupted (e.g., the brain stem near a tumor to be necrotized).

Accordingly, the environment 200 includes the tissue damage analysis computer system 230, which is configured to analyze both the temperature and duration of applied temperature associated with multiple locations of tissue affected by a laser ablation device (e.g., laser ablation device 220). In addition, the tissue damage analysis computer system 230 may be configured to assist an end user (e.g., a physician) in avoiding unintentionally disrupting tissue located near target tissue (e.g., by automatically shutting off power to the ablation device, by lowering the temperature applied to target tissue, by warning the end user of potential unintentional damage, and so forth), as further described herein.

As shown in FIG. 2, the tissue damage analysis computer system 230 may include various engines, functional blocks, and components, including a temperature analysis engine 232, a duration analysis engine 234, a user interface (UI) engine 236, and a structures and rules engine 238, each of which may also include additional engines, functional blocks, and components (not shown). As such, the configuration of the tissue damage analysis computer system 230 illustrated in FIG. 2 is shown only for exemplary purposes.

Figure 3:
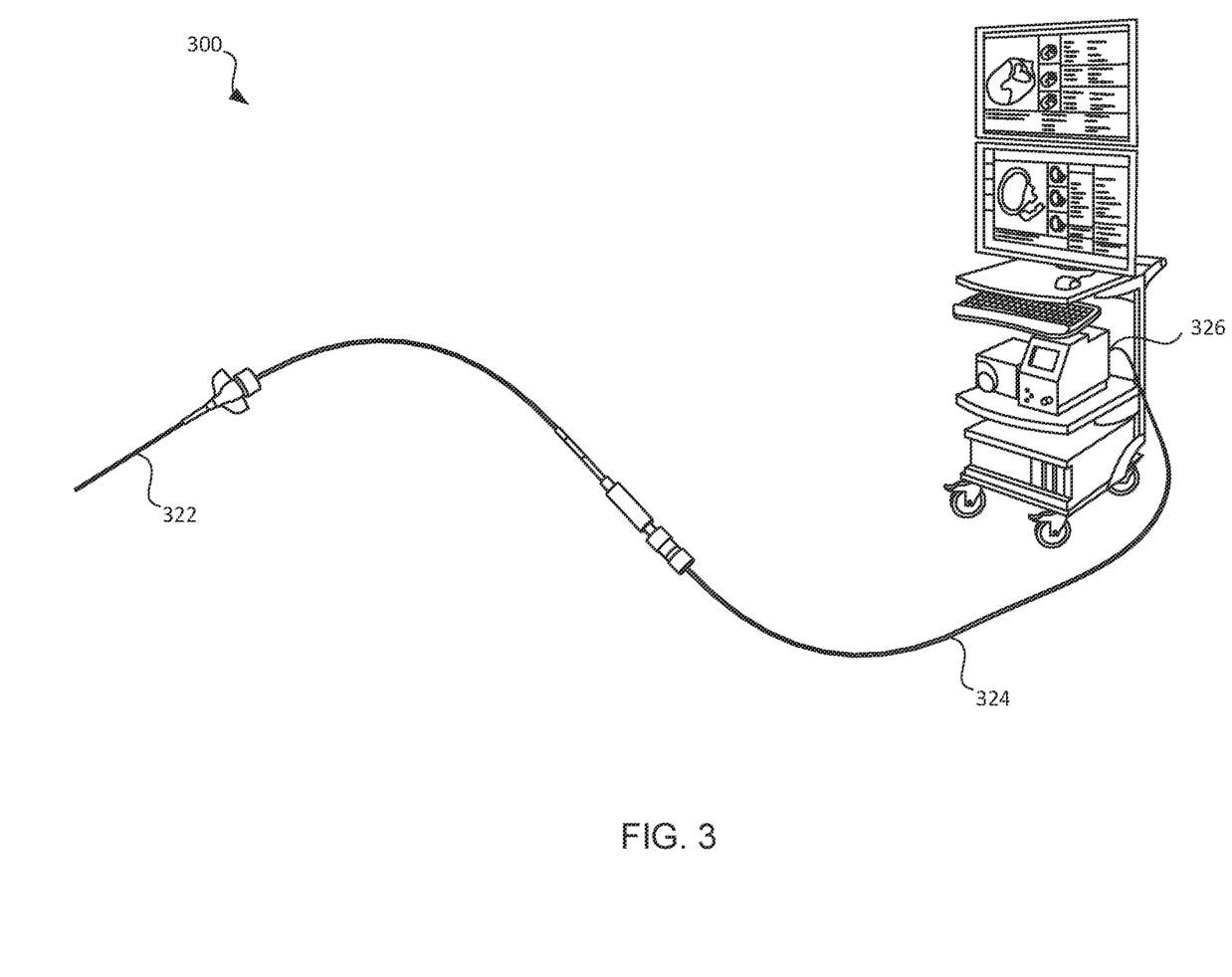
FIG. 3 illustrates an example system, according to one embodiment, for performing a laser ablation procedure.

The temperature analysis engine 232 may be configured to measure and monitor the temperature of various objects of tissue in addition to the target tissue in real-time during an ablation procedure. Such measurements and monitoring may be performed by utilizing various technologies. In an example, the temperature analysis engine may utilize proton resonance frequency (PRF) MRI thermometry. In another example, a probe (e.g., the laser applicator 322) used during a procedure may include one or more physical temperature sensors that are configured to monitor the temperature of nearby tissue.

Notably, the objects of tissue being monitored by the temperature analysis engine may be any definable object or structure of tissue. For instance, the temperature analysis engine may monitor the temperature at various zones or voxels correlated to tissue. In addition, such objects may include user-defined objects that are defined through software, computer-defined objects that are defined through machine learning, tissue structures identified by the tissue damage analysis computer system based on pre-defined objects (e.g., via the structures and rules engine 238), and so forth. In a specific example, such objects may comprise brain fiber tracts viewable through diffusion tensor imaging (DTI). In another example, a model of an object or structure may be built by a user by hand or created by a computer system (e.g., via the structures and rules engine 238, as further described herein). In a more particular example, an end user (e.g., a physician) may create an object of tissue to be monitored for temperature using a surgical planning software such as a StealthStation™ (or via the UI engine 236).

As briefly described, the tissue damage analysis computer system 230 also includes the duration analysis engine 234. The duration analysis engine may be configured to determine the duration at which any given tissue (e.g., structures, objects, voxels, zones, and so forth, as further described herein) has been placed at an elevated temperature. In other words, the tissue duration analysis engine may determine the thermal dose (the accumulated thermal energy) that has been applied to any given tissue during a procedure. In some embodiments, the duration analysis engine may utilize one or more models that assist in making such determinations. For instance, the Arrhenius model may be used to assist in determining the duration at which any given tissue has been placed at an elevated temperature. In another example, the cumulative equivalent minutes at 43° C. (CEM43) model may be used to assist in making such determinations. While two examples of particular models are discussed, any model that assists in estimating both temperature and duration (e.g., amount of time at an elevated temperature) may be used.

Figure 4:
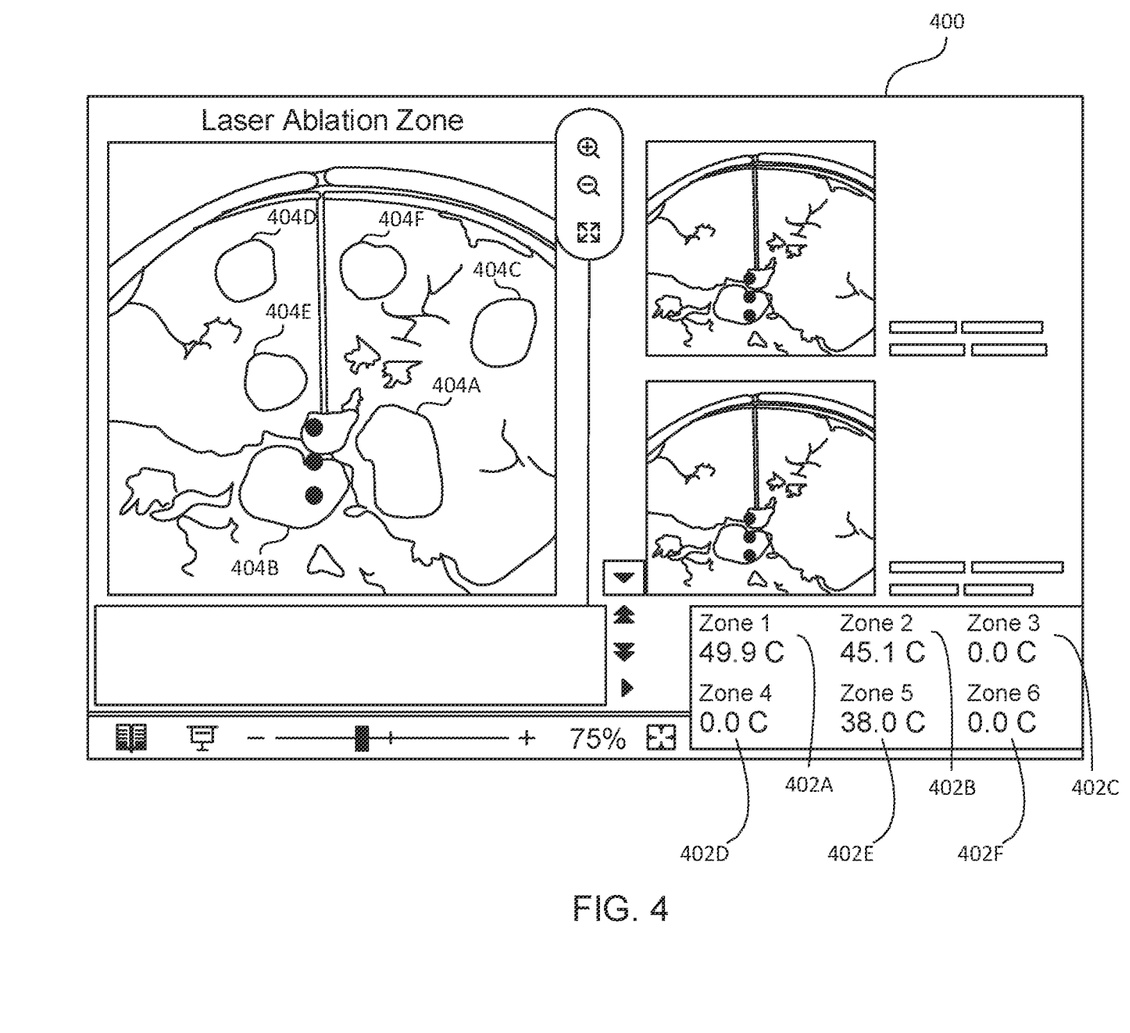
FIG. 4 illustrates an example user interface, according to one embodiment, for protecting non-target tissue from damage during a medical procedure for disrupting tissue via heat application.

As illustrated in FIG. 2, the tissue damage analysis computer system also includes the UI engine 236. The UI engine 236 may be configured to allow an end user (e.g., a physician) to perform numerous tasks during a procedure related to monitoring elevated temperatures of tissue. For instance, the UI engine 236 may allow an end user to view one or more images of objects of tissue (e.g., zones, voxels, and so forth) in conjunction with a corresponding temperature or thermal dose of the tissue. For instance, FIG. 4 illustrates an example UI 400 of the UI engine 236, which includes six separate zones of tissue 404 (i.e., 404A through 404F) that are each being monitored with respect to temperature by the temperature analysis engine 232. As illustrated, temperatures corresponding to each zone of tissue 404 are shown as temperatures 402 (i.e., 402A through 402F). While six tissue zones are shown in FIG. 4, any number of objects (e.g., user-created objects, voxels, and so forth) may be monitored with respect to temperature and/or thermal dose. Similarly, while only temperature is shown, a current thermal dose for each zone 404 may also be illustrated within the UI 400. In addition to showing numerical values for temperature and thermal dose, both temperature and thermal dose may be shown using colors (e.g., red for temperatures/thermal doses nearing a threshold, blue for temperatures/thermal doses that are not near a given threshold, and so forth). Similarly, temperature and thermal dose may also be identified audibly by stating temperatures/thermal doses of particular zones, stating that thresholds are being approached, and so forth. While particular examples are discussed herein, any visual or audible indicia may be used with respect to the temperature and thermal dose (as well as any thresholds associated with such) of any given tissue structure.

In addition to presenting images of tissue and corresponding temperatures/thermal doses, the UI engine 236 may be configured to receive various types of input from an end user. For instance, the UI engine 236 receive input from an end user regarding the particular tissue objects to be monitored. In another example, the UI engine may also allow an end user to identify and create particular objects of tissue (e.g., voxels, zones, and so forth) to be monitored. In yet another example, the UI engine may allow an end user to modify temperature/thermal dose thresholds (as they are further described herein) before, during, or after a given procedure. In yet another example, the UI engine may allow an end user to input information regarding target tissue and non-target tissue, including recommended thresholds, characteristics of types/subtypes of tissue (e.g., temperatures and thermal doses at which damage begins to occur to such tissue types), the type of responses to be performed when a given threshold has been met, and so forth.

As briefly described, the tissue damage analysis engine also includes the structures and rules engine 238. The structures and rules engine may store and analyze a number of tissue structures and rules related to such tissue structures. For instance, the structures and rules engine may be able to identify and analyze various types of tissue (e.g., brain tissue, skin tissue, kidney tissue, liver tissue, and so forth). The structures and rules engine may further be able to identify and analyze various subtypes of tissue. More specifically, the structures and rules engine may be able to identify and analyze particular types of brain tissue (e.g., the brain stem), skin tissue, kidney tissue, liver tissue, and so forth.

As part of such analyses, the structures and rules engine may (in conjunction with the temperature analysis engine and/or the duration analysis engine) be able to determine the maximum temperature and maximum thermal dose that any given tissue type or subtype can withstand before damage to such tissue begins to occur. Based at least partially on these analyses, the tissue damage analysis computer system (and/or one of its engines) may allow for performing a number of functions. For instance, thresholds related to the maximum temperature and/or maximum thermal dose of any given tissue type or subtype may be created for purposes of providing notifications or alerts to an end user (e.g., a physician performing a laser ablation procedure); reducing the amount of heat provided by the heat source; or automatically shutting off one or more devices during a procedure (e.g., the laser energy source during a laser ablation procedure). For instance, when a non-target object of tissue (i.e., a portion of tissue not intentionally being necrotized) that is being monitored by the temperature analysis engine and/or the duration analysis engine reaches a temperature or thermal dose at which necrotization may occur (i.e., a temperature or thermal dose threshold associated with the non-target tissue), the tissue damage analysis computer system may cause one or more devices or pieces of equipment (e.g., the source of heat) to automatically shut off.

Such thresholds may be created in a number of different forms. For instance, thresholds for any given tissue type or subtype may be created based on a percent likelihood of damage or on a criticality of the tissue type or subtype. For instance, a threshold for the brain stem may automatically be created to be very conservative (e.g., between 25 and 35 degrees below the temperature at which tissue disruption occurs) because of the importance of the tissue. As such, thresholds may also comprise qualitative identifiers such as conservative, most conservative, least conservative, aggressive, and so forth. In particular, more conservative thresholds may comprise temperatures/thermal doses that are well below the temperatures/thermal doses at which corresponding tissue objects will necrotize. On the other hand, less conservative or aggressive thresholds may comprise temperatures/thermal doses that are at or near the temperatures/thermal doses at which corresponding tissue objects will necrotize or become disrupted.

Notably, such thresholds may automatically be created by the tissue damage analysis computer system based on an analysis of one or more factors, including but not limited to the importance of fully disrupting the target tissue, the criticality of potentially affected non-target tissue, the temperature and/or thermal dose at which the target tissue will necrotize, the temperature and/or thermal dose at which potentially affected non-target tissue will necrotize, the type of procedure being performed, and so forth. For instance, the structures and rules engine may automatically analyze and identify the target tissue and potentially affected objects of non-target tissue based on a type of procedure being performed. Based on such analyses, the structures and rules engine may further consider the importance of necrotizing the target tissue, the criticality of the potentially affected tissue, and the temperature/thermal dose at which necrotization will occur to the potentially affected tissue in comparison to the target tissue. Such analyses and considerations may then be used to generate a threshold temperature and/or thermal dose when a response is to be performed (e.g., sending an alert/notification, lowering heat, shutting off devices, and so forth). As an example, based on determining that potentially affected non-target tissue is critically important, a very conservative threshold may be generated. In another example, a least conservative (or aggressive) threshold may be generated in response to identifying that the target tissue of a given procedure is an advanced malignant tumor.

End users may also be able to generate, modify, or even eliminate temperature/thermal dose thresholds. For instance, the UI engine 236 may allow a user to modify thresholds for any given object of tissue being monitored. In addition, an end user may be able to provide information that can assist the structures and rules engine in generating a threshold for any given tissue. As an example, an end user may be able to identify known objects of tissue near target tissue for a given procedure that may be unintentionally affected by heat applied to the target tissue. Based at least partially on such identification, the structures and rules engine may generate an appropriate threshold for each identified object of tissue. In some embodiments, the UI engine 236 may request that an end user provide any known potentially affected critical tissue for a procedure to be performed.

As described above, there may be situations where equipment is shut off during a procedure (i.e., before the procedure is finished) to protect one or more objects of tissue. In such situations, it may be necessary for the physician performing the procedure to eventually resume and finish the procedure. In such instances, the duration analysis engine may be configured to consider the thermal dose absorbed by all tissue objects affected during all portions of the procedure, regardless of the number of times the procedure is stopped and started again. As an example, during a laser ablation procedure, assume the laser energy source has automatically shut off based on determining that the temperature or thermal dose of a non-target object of tissue has reached its corresponding generated threshold. Also assume that the target tissue must be necrotized, which has not yet occurred. When resuming the procedure and until the procedure is complete, the duration analysis engine may consider the thermal dose absorbed by the non-target tissue during the initial portion of the procedure (i.e., the portion of the procedure prior to automatically shutting off the laser energy source) when determining the total thermal dose absorbed by the non-target object of tissue.

Notably, the end user may also be able to modify the threshold corresponding to any given object of tissue to ensure that the procedure can achieve its intended goal. In an example, if the generated threshold for a given non-target object of tissue is initially very conservative and the heat energy source is shut off well before necrotizing a target object of tissue, the end user may be able to adjust the threshold. For instance, a physician may adjust the threshold in situations where disrupting the target tissue is determined to be more important to the patient's well-being than protecting the affected non-target tissue.

Figure 5:
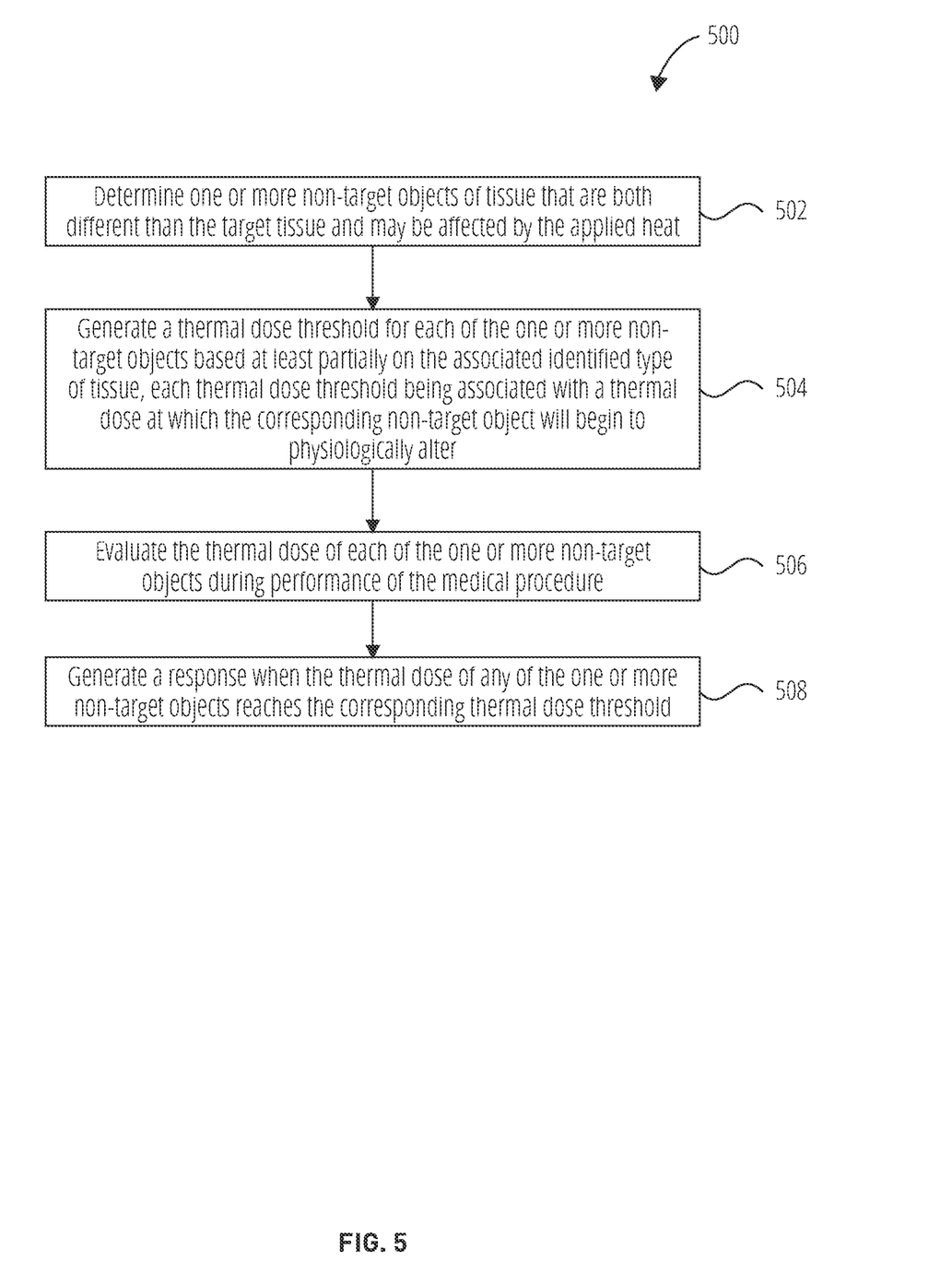
FIG. 5 illustrates a flowchart of a method, according to one embodiment, for protecting non-target tissue from damage during a medical procedure for disrupting tissue via heat application.

FIG. 5 illustrates a flowchart of a method 500 for protecting non-target tissue from damage during a medical procedure for applying heat to a target tissue. The method 500 is described with frequent reference to the environment of FIG. 2. The method 500 includes determining one or more non-target objects of tissue that are both different than the target tissue and may be affected by the applied heat (Act 502). For instance, the structures and rules engine 238 may be configured to determine or identify one or more structures of non-target tissue that may be affected when performing a procedure on the particular target tissue. Notably, identifying the one or more non-target objects may include identifying a type of tissue associated with each of the one or more identified non-target objects. For example, the structures and rules engine 238 may identify that non-target tissue comprises brain tissue, skin tissue, liver tissue, and so forth. Subtypes of tissue may also be identified (e.g., the brainstem, which comprises a brain tissue type).

The method 500 further includes generating a thermal dose threshold for each of the one or more non-target objects based at least partially on the associated identified type of tissue (Act 504). As an example, the structures and rules engine 238 may generate both a temperature threshold and a thermal dose threshold for each non-target object of tissue based at least partially on the type of each non-target tissue, which thresholds may be used for generating automatic responses when reached during a procedure. Notably, each temperature threshold may be associated with a thermal dose at which the corresponding non-target object will begin to physiologically alter (e.g., necrosis, opening blood/brain barrier, and so forth).

The method 500 also includes evaluating the thermal dose of each of the one or more non-target objects during performance of the medical procedure (Act 506). For instance, the duration analysis engine may evaluate the thermal dose absorbed by non-target tissue (and target tissue) during the procedure. In addition, the temperature analysis engine 232 may evaluate the temperature of non-target tissue (and target tissue) during the procedure. The method 500 further includes generating a response when the thermal dose of any of the one or more non-target objects reaches the corresponding thermal dose threshold (Act 508). As an example, the structures and rules engine may cause a response to occur when a threshold has been met, including sending an alert to an end user (e.g., a physician), reducing the heat energy supplied by a heat energy source, or shutting off the heat energy source.

Accordingly, the principles described herein may allow for protecting non-target tissue during a procedure that utilizes heat to disrupt target tissue by evaluating both the temperature of non-target tissue and the thermal dose absorbed by non-target tissue. In this way, critical tissue structures (e.g., the brain stem) near target tissue (e.g., a malignant brain tumor) may be protected even when disrupting nearby tissue. Notably, without the thermal dose being evaluated, critical tissue at even low-levels of elevated temperature may be damaged or disrupted when heat has been applied for relatively long periods of this time. As such, the principles described herein provide much more robust protection for critical tissue structures during a procedure that applies heat to tissue than methods and systems that merely monitor for temperature.

Although the subject matter has been described in language specific to structural features and/or methodological acts, it is to be understood that the subject matter defined in the appended claims is not necessarily limited to the described features or acts described above, or the order of the acts described above. Rather, the described features and acts are disclosed as example forms of implementing the claims.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to an "embodiment" means that a particular feature, structure, or characteristic described in connection with that embodiment is included in at least one embodiment. Thus, references to embodiments throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

The invention claimed is:

1. A computer system comprising:
one or more processors; and
one or more non-transitory computer-readable storage media having stored thereon computer-executable instructions that are executable by the one or more processors to cause the computer system to protect non-target tissue from damage during a medical procedure for applying heat to a target tissue, the computer-executable instructions including instructions that are executable to cause the computer system to perform at least the following:
receive images of a zone of tissue comprising the non-target tissue and the target tissue;
determine, based on the images of the zone of tissue, one or more non-target objects of tissue that are both different than the target tissue and that are susceptible to damage from an amount of the heat applied to the target tissue;
identify, based on the images of the zone of tissue, a type of tissue associated with each of the one or more non-target objects of tissue;
determine, based at least partially on the type of tissue identified, a temperature threshold for each of the one or more non-target objects of tissue, wherein the temperature threshold comprises a first temperature for each of the one or more non-target objects of tissue at which a corresponding non-target object of the type of tissue identified is damaged quickly in a first amount of time;
determine, based at least partially on the type of tissue identified, a thermal dose threshold for each of the one or more non-target objects of tissue, wherein the thermal dose threshold corresponds to an accumulation of thermal energy over time at which the corresponding non-target object of the type of tissue identified begins to physiologically alter when a second temperature is applied to the corresponding non-target object of the type of tissue identified over a second amount of time, wherein the second temperature is less than the first temperature, and wherein the second amount of time is greater than the first amount of time;
determine, based on measurements received from a temperature sensor, a temperature at each of the one or more non-target objects of tissue during performance of the medical procedure;
determine, based on the temperature determined and the heat applied to the target tissue, an amount of accumulated thermal energy of each of the one or more non-target objects of tissue during performance of the medical procedure when the temperature at each of the one or more non-target objects of tissue determined to be lower than the first temperature, wherein the amount of accumulated thermal energy comprises the temperature at each of the one or more non-target objects of tissue and a duration that the temperature at each of the one or more non-target objects of tissue is applied over a period of time during performance of the medical procedure;

cause a representation of the amount of accumulated thermal energy of each of the one or more non-target objects of tissue to be rendered to a user interface of a display device during performance of the medical procedure; and cause a response alert to be output by the computer system when the amount of accumulated thermal energy of any of the one or more non-target objects of tissue reaches the thermal dose threshold for the corresponding non-target object of the type of tissue identified.

2. The computer system of claim 1, wherein the medical procedure comprises a laser ablation procedure.

3. The computer system of claim 1, wherein determining the one or more non-target objects of tissue includes identifying a subtype of tissue associated with each of the one or more non-target objects of tissue identified.

4. The computer system of claim 1, wherein the computer-executable instructions further include instructions that are executable to cause the computer system to:

cause a damage response alert to be output by the computer system when the temperature of any of the one or more non-target objects reaches the temperature threshold for the corresponding non-target object of type of tissue identified.

5. The computer system of claim 1, wherein the type of tissue identified for at least one of the one or more non-target objects of tissue comprises brain tissue, kidney tissue, liver tissue, or skin tissue.

6. The computer system of claim 1, wherein the computer-executable instructions further include instructions that are executable to cause the computer system to:

determine a tissue structure of at least one of the one or more non-target objects of tissue to determine a criticality associated with the at least one of the one or more non-target objects of tissue, wherein the criticality defines an importance of the at least one of the one or more non-target objects of tissue relative to other non-target objects of tissue; and adjust, based on the criticality, an output of the heat applied to the target tissue during the medical procedure from a first energy level to a second energy level, wherein the second energy level is lower than the first energy level.

7. The computer system of claim 1, wherein, when the amount of accumulated thermal energy of any of the one or more non-target objects of tissue reaches the thermal dose threshold for the corresponding non-target object of the type of tissue identified, the computer-executable instructions further include instructions that are executable to cause the computer system to automatically reduce an amount of heat applied to the target tissue.

8. The computer system of claim 1, wherein the computer-executable instructions further include instructions that are executable to cause the computer system to determine the amount of accumulated thermal energy of each of the one or more non-target objects of tissue after a heat source generating the heat has stopped and restarted based at least in part on an amount of time that each of the one or more non-target objects of tissue absorbed the heat before the heat source stopped and before the heat source restarted.

9. The computer system of claim 1, wherein the computer-executable instructions further include instructions that are executable to cause the computer system to:

receive, in real time, data associated with the target tissue during the medical procedure; and determine, based on the data received, the one or more non-target objects of tissue.

10. The computer system of claim 1, wherein the thermal dose threshold for each of the one or more non-target objects of tissue is associated with an accumulation of thermal energy at which the corresponding non-target object of the type of tissue identified begins to physiologically alter by necrosis.

11. The computer system of claim 1, wherein the thermal dose threshold for each of the one or more non-target objects of tissue is associated with an accumulation of thermal energy at which the corresponding non-target object of the type of tissue identified begins to physiologically alter by opening a blood-brain barrier.

12. A method for protecting non-target tissue from damage during a medical procedure for applying heat to a target tissue, comprising:

determining, by one or more processors based on images received of a zone of tissue, one or more non-target objects of tissue that are both different than the target tissue and that are susceptible to damage from an amount of the heat applied to the target tissue;

identifying, by the one or more processors based on the images received of the zone of tissue, a type of tissue associated with each of the one or more non-target objects of tissue;

determining, by the one or more processors, a temperature threshold for each of the one or more non-target objects of tissue, wherein the temperature threshold comprises a first temperature for each of the one or more non-target objects of tissue at which a corresponding non-target object of the type of tissue identified is damaged quickly in a first amount of time;

determining, by the one or more processors, a thermal dose threshold for each of the one or more non-target objects of tissue based at least partially on the type of tissue identified, wherein the thermal dose threshold corresponds to an accumulation of thermal energy over time at which a the corresponding non-target object of the type of tissue identified begins to physiologically alter when a second temperature is applied to the corresponding non-target object of the type of tissue identified over a second amount of time, wherein the second temperature is less than the first temperature, and wherein the second amount of time is greater than the first amount of time;

determining, by the one or more processors based on measurements received from a temperature sensor, a temperature at each of the one or more non-target objects of tissue during performance of the medical procedure;

determining, by the one or more processors based on the temperature determined and the heat applied to the target tissue, an amount of accumulated thermal energy of each of the one or more non-target objects of tissue during performance of the medical procedure when the temperature at each of the one or more non-target objects of tissue determined to be lower than the first temperature, wherein the amount of accumulated thermal energy comprises the temperature at each of the one or more non-target objects of tissue and a duration that the temperature at each of the one or more non-target objects of tissue is applied over a period of time during performance of the medical procedure;

causing, by the one or more processors, a representation of the amount of accumulated thermal energy of each of the one or more non-target objects of tissue to be rendered to a user interface of a display device during performance of the medical procedure; and causing, by the one or more processors, a response alert to be output when the amount of accumulated thermal energy of any of the one or more non-target objects of tissue reaches the thermal dose threshold for the corresponding non-target object of the type of tissue identified.

13. The method of claim 12, wherein the medical procedure comprises a laser ablation procedure.

14. The method of claim 12, wherein the type of tissue identified for at least one of the one or more non-target objects of tissue comprises brain tissue, kidney tissue, liver tissue, or skin tissue.

15. The method of claim 12, further comprising:
determining, by the one or more processors, a tissue structure of at least one of the one or more non-target objects of tissue to determine a criticality associated with the at least one of the one or more non-target objects of tissue, wherein the criticality defines an importance of the at least one of the one or more non-target objects of tissue relative to other non-target objects of tissue; and adjusting, by the one or more processors based on the criticality, an output of the heat applied to the target tissue during the medical procedure from a first energy level to a second energy level, wherein the second energy level is lower than the first energy level.

16. The method of claim 12, further comprising:
causing an amount of heat applied to the target tissue to be reduced when the amount of accumulated thermal energy of any of the one or more non-target objects of tissue reaches the thermal dose threshold for the corresponding non-target object of the type of tissue identified.

17. A computer program product comprising one or more non-transitory computer readable media having stored thereon computer-executable instructions that are executable by one or more processors of a computer system to cause the computer system to protect non-target tissue from damage during a medical procedure for applying heat to a target tissue, the computer-executable instructions including instructions that are executable to cause the computer system to perform at least the following:

receive images of a zone of tissue comprising the non-target tissue and the target tissue;

determine, based on the images of the zone of tissue, one or more non-target objects of tissue that are both different than the target tissue and that are susceptible to damage from an amount of the heat applied to the target tissue;

identify, based on the images of the zone of tissue, a type of tissue associated with each of the one or more non-target objects of tissue;

determine, based at least partially on the type of tissue identified, a temperature threshold for each of the one or more non-target objects of tissue, wherein the temperature threshold comprises a first temperature for each of the one or more non-target objects of tissue at which a corresponding non-target object of the type of tissue identified is damaged quickly in a first amount of time;

determine, based at least partially on the type of tissue identified, a thermal dose threshold for each of the one or more non-target objects of tissue, wherein the thermal dose threshold corresponds to an accumulation of thermal energy over time at which the corresponding non-target object of the type of tissue identified begins to physiologically alter when a second temperature is applied to the corresponding non-target object of the type of tissue identified over a second amount of time, wherein the second temperature is less than the first temperature, and wherein the second amount of time is greater than the first amount of time;

determine, based on measurements received from a temperature sensor, a temperature at each of the one or more non-target objects of tissue during performance of the medical procedure;

determine, based on the temperature determined and the heat applied to the target tissue, an amount of accumulated thermal energy of each of the one or more non-target objects of tissue during performance of the medical procedure, wherein the amount of accumulated thermal energy comprises the temperature at each of the one or more non-target objects of tissue and a duration that the temperature at each of the one or more non-target objects of tissue is applied over a period of time during performance of the medical procedure when the temperature at each of the one or more non-target objects of tissue determined to be lower than the first temperature;

cause a representation of the amount of accumulated thermal energy of each of the one or more non-target objects of tissue to be rendered to a user interface of a display device during performance of the medical procedure; and cause a response alert to be output when the amount of accumulated thermal energy of any of the one or more non-target objects of tissue reaches the thermal dose threshold for the corresponding non-target object of the type of tissue identified.

18. The computer program product of claim 17, wherein the computer-executable instructions further include instructions that are executable to cause the computer system to:
cause a damage response alert to be output by the computer system when the temperature of any of the one or more non-target objects reaches the temperature threshold for the corresponding non-target object of type of tissue identified.

19. The computer program product of claim 17, wherein the thermal dose threshold for each of the one or more non-target objects of tissue is associated with an accumulation of thermal energy at which the corresponding non-target object of the type of tissue identified begins to necrotize.

20. The computer program product of claim 19, wherein a temperature threshold for each of the one or more non-target objects of tissue is associated with a temperature at which the corresponding non-target object of the type of tissue identified begins to open a blood-brain barrier.

21. The method of claim 12, further comprising:
causing, by the one or more processors, a damage response alert to be output by a computer system when the temperature of any of the one or more non-target objects reaches the temperature threshold for the corresponding non-target object of type of tissue identified.

\* \* \* \* \*